(12) United States Patent
Perez et al.

(10) Patent No.: US 7,112,719 B2
(45) Date of Patent: Sep. 26, 2006

(54) USE OF MALE STERILITY TO PREVENT TRANSGENE SPREAD IN PLANTS

(75) Inventors: Pascual Perez, Chanonat (FR); Pascal Flament, Cinq Ormes Houville (FR)

(73) Assignee: Biogemma, Paris (FR)

( * ) Notice: Subject to any disclaimer, the term of this patent is extended or adjusted under 35 U.S.C. 154(b) by 0 days.

(21) Appl. No.: 09/380,086

(22) PCT Filed: Feb. 26, 1998

(86) PCT No.: PCT/FR98/00381

§ 371 (c)(1),
(2), (4) Date: Nov. 29, 1999

(87) PCT Pub. No.: WO98/38323

PCT Pub. Date: Sep. 3, 1998

(65) Prior Publication Data

US 2002/0157129 A1    Oct. 24, 2002

(30) Foreign Application Priority Data

Feb. 27, 1997    (FR) .................................. 97 02369

(51) Int. Cl.
*C12N 15/82*    (2006.01)
(52) U.S. Cl. ..................................... 800/288
(58) Field of Classification Search ............... 800/278, 800/287, 288, 290, 303, 317.4, 320.1, 317.3, 800/306, 274; 435/410, 411, 412, 414, 419
See application file for complete search history.

(56) References Cited

U.S. PATENT DOCUMENTS

| | | | | |
|---|---|---|---|---|
| 5,180,873 A | * | 1/1993 | Jorgensen | 800/205 |
| 5,451,513 A | * | 9/1995 | Maliga et al. | 435/172.3 |
| 5,689,041 A | * | 11/1997 | Mariani et al. | 800/205 |
| 5,712,135 A | * | 1/1998 | D'Halluin et al. | 800/292 |
| 5,728,558 A | * | 3/1998 | Fabijanski et al. | 435/172.3 |
| 6,573,431 B1 | * | 6/2003 | Lenee et al. | 800/295 |

FOREIGN PATENT DOCUMENTS

| | | | |
|---|---|---|---|
| EP |  | 344029 | * 8/1996 |
| WO | WO | 96/26283 | * 11/1989 |
| WO | WO | 91/09957 | 7/1991 |
| WO | WO | 92/11379 | 7/1992 |
| WO | WO | 93/01283 | 1/1993 |
| WO | WO | 93/02197 | 2/1993 |
| WO | WO | 96/15252 | 5/1996 |
| WO | WO | 98/06861 | * 2/1998 |

OTHER PUBLICATIONS

Gray A. J. and Raybould A. F, "Reducing transgene escape routes." 1998, NATURE, vol. 392, pp. 653-654.*
Worrall, D. et al., "Premature Dissolution of the Microsporocyte Callose Wall Causes Male Sterility in Transgenic Tobacco." 1992, The Plant Cell, vol. 4, pp. 759-771.*
Paul, W. et al., "The isolation and characterisation of the tapetum-specific *Arabidopsis thaliana* A9 gene." 1992, Plant Molecular, Biology, vol. 19, pp. 611-622.*
Nyers, L. S. et al., "Genetic Engineering of Reversible Sterility in Trees: Approaches, Problems and Progress." 1991, J. Cell Biochem, vol. 15A, pp. 136.*
Svab et al. Stable transformation of plastides in higher plants, 1990. Proc. Natl. Acad. Set, vol. 87, pp. 8526-8530.*
Metz et al, 1995, Mol. Breed. 1:309-317.*
Vedel et al, 1994, Plant Physiol. Biochem. 32:601-618.*
Norman C. Ellstrand et al., "Hybridization As An Avenue Of Escape For Engineered Genes", Bioscience vol. 40, No. 6, Jun. 1990, pp. 438-442.

* cited by examiner

*Primary Examiner*—Anne Kubelik
(74) *Attorney, Agent, or Firm*—Young & Thompson (57) ABSTRACT

The invention relates to a method for preventing the spread via pollen of a transgene encoding dog gastric lipase or collagen from transgenic plants comprising said transgene. In this method plants are transformed with a construct comprising the transgene genetically linked to a second construct conferring male sterility on the plant. Plants produced by the method are male sterile, and thus cannot spread the transgene via their pollen.

7 Claims, 1 Drawing Sheet

Location of oligonucleotides A9a and A9b

FIG. 1

Location of oligonucleotides EM1 and EM5

FIG. 2

Location of oligonucleotides 5'H and Ac12

FIG. 3

USE OF MALE STERILITY TO PREVENT TRANSGENE SPREAD IN PLANTS

BACKGROUND OF THE INVENTION

1. Field of the Invention

The invention relates to novel uses of male sterility for limiting the risks to humans and the environment which are linked to producing transgenic plants.

2. Description of the Related Art

The benefits of using transgenic plants are very promising. The transgenesis of mammalian genes into a plant cell offers, in particular, a route for producing novel recombinant proteins in large quantities at a reduced production cost and without the risk of viral or subviral (prion) contamination.

However, these benefits should not cause the aspects of an ecological nature which are linked to producing transgenic plants and to which the public is very sensitive to be forgotten.

The applicant has now developed a technology which places male sterility at the service of a "green biotechnology" which takes into consideration ecological and human aspects.

A possible improvement resides in controlling the dissemination of the transgene in the environment.

While the spatial isolation of culture plots already makes it possible to reduce the risk of the transgene "escaping", this method is restricting and becomes problematical as the number of products increases.

The significance of genetic methods for isolating the transgene and reducing the risk of an "escape", was suggested in an article by Ellstrand in 1990. Among the large number of proposed solutions in the face of the problem of the "escape" of the transgene, Ellstrand notes that male-sterile genotypes could be introduced or that a gene which was lethal for the pollen could be linked directly to a gene which was constructed by genetic engineering. However, no technical development had been implemented in this sense. In fact, it was impossible to foresee such a development being implemented successfully on account, in particular, of the number of parameters which are brought into play in the genetic engineering techniques used in plants.

SUMMARY OF THE INVENTION

The applicant has developed a technology which makes it possible to prevent the transgene being disseminated by way of the pollen and therefore to prevent the transgene "escaping" into the environment, according to which technology a male-sterile plant is used for avoiding the dissemination of a transgene of interest which is integrated into the genome of the said plant.

It is known that controlling male fertility is of importance for the production of hybrid plants which involves crossing two different lines.

One of the methods for preventing self fertilization by controlling pollination is manual "castration" of the male organs of the plant.

Research has also been carried out into the possibility of controlling development of the pollen genetically.

Male sterility can be "acquired", that is independently of any genetic manipulation whatsoever, by the recombinant DNA route. It is possible to distinguish cytoplasmic male sterility from nuclear male sterility (Williams, 1995). Cytoplasmic male sterility is linked to changes in the organization and expression of the mitochondrial genome, while nuclear male sterility results from mutations in the genome of the nucleus of the cell.

Male sterility can also be "artificial", that is induced by the expression of a gene which confers male sterility (AMS gene) and which is inserted either in the mitochondrial genome (cytoplasmic male sterility) or in the nuclear genome (nuclear male sterility).

In accordance with the invention, the said male-sterile plant which is used for avoiding dissemination of a transgene of interest which is integrated into the genome of the said plant carries:

either a cytoplasmic male sterility, preferably an artificial male sterility which is induced by a transgene which is integrated into the mitochondrial genome of the said plant;

or a nuclear male sterility, preferably a male sterility which is induced by a transgene which is inserted into a non-essential site of the nuclear genome of the said plant.

Preferably, in accordance with the invention, the said plant can have been rendered male-sterile by the insertion, into a non-essential site of the nuclear genome, of a sequence which comprises an AMS gene and the said transgene of interest, with these genes being genetically linked.

The link between the gene of interest and the gene for AMS will have the effect of preventing its dissemination by the pollen route, thereby permitting a large number of different products to be produced in one and the same environment.

In addition, the transfer of the AMS gene itself into wild-type plants is not to be feared since it will not be capable of being retained within a wild-type population to the extent that it represents more of a "genetic burden" than any selective advantage whatsoever.

A link between the gene of interest and the AMS gene is understood as being a genetic distance which is sufficiently short for the frequencies of recombination during meiosis to be negligible.

By means of genetic transformation, it is possible to introduce, into a plant, two, if not three, genes whose physical linkage is absolute.

The invention also relates to a transgenic plant or to a part or extract of a transgenic plant, characterized in that the said transgene of interest is genetically linked to an AMS gene which is combined with elements which enable it to be expressed in plant cells, in particular a promoter and a transcription terminator.

In accordance with the present invention, it is understood that the presence of the said AMS gene does not prevent the said transgene of interest from being expressed.

A "part" of a transgenic plant is understood, in particular, as being the leaves, fruits or cells of genetically transformed plants.

The invention also relates to a vector, in particular a plasmid, which is characterized in that it contains a transgene of interest which is combined with elements which enable it to be expressed in plant cells, in particular a promoter and a transcription terminator, and which is genetically linked to an AMS gene which is combined with elements which enable it to be expressed in plant cells, in particular a promoter and a transcription terminator.

According to one preferred embodiment of the invention, the artificial male sterility can be conferred by a gene which consists of a sequence which encodes a protein which is able to degrade the cellular RNA molecules (RNAse) under the control of a specific anther promoter, as described by PAUL W. et al. (1992).

This RNAse can be *Bacillus amyloliquefaciens* Barnase. The promoter can advantageously be the *Arabidopsis thaliana* A9 promoter, which is specific for the anther tapetum.

The plants which express this chimeric gene become unable to produce viable pollen due to specific destruction of the cells of the anther carpet. These plants are otherwise normal.

Since the plants according to the invention are unable to produce viable pollen, there is no risk of disseminating the male sterility gene and the gene of interest with the pollen.

These plants are replicated by supplying pollen which comes from plants which do not carry the gene of interest according to the invention.

In the case of maize, cultivating the transgenic plants with a view to production can be ensured in accordance with a scheme of the seed production type (4 or 6 female lines followed by 2 pollinating lines). The plants which are used as females (plants which carry the gene of interest) are sown at double density. In such a scheme, the gene of interest is linked to a selection gene (for example a gene which confers resistance to a herbicide), thereby subsequently making it possible, by means of treating with the selective agent (herbicide, for example), to eliminate the plants other than the male-sterile plants. It is then only the female lines which are harvested.

A mixed sowing can also be envisaged for the final production. In this case, the pollinating line does not carry the gene of interest and is used in a mixture (10%) with the line which is used as the female line. The sowing is carried out at double density. In this case, the whole of the field is harvested.

According to another embodiment of the invention, use is made of cytoplasmic male sterility for limiting dissemination of a transgene which is integrated into the genome of a plant.

Plants which carry cytoplasmic male sterility are affected in their mitochondrial genome which makes them incapable of producing pollen in the absence of nuclear genes which restore this property. This male sterility can either be "acquired" or induced artificially by inserting, into the mitochondrial genome, a gene which confers cytoplasmic male sterility (CMS gene), for example the Ogura gene.

Such plants are normally used by seed companies to facilitate their production of seeds. For example, a substantial part of the production of maize seeds in Europe is based on using so-called type C cytoplasmic male sterility.

According to a preferred embodiment of the invention, a transgene is introduced by back-crossing in a plant line, in particular a maize plant line, which carries cytoplasmic male sterility. In this case, the male-sterile plant is used as the female parent. Two successive back-crossings followed by assessments and selections in the progeny make it possible to achieve the homozygous state for this transgene.

In the absence of a nuclear restoration gene (Rf4 gene in the case of C cytoplasm), the plant carrying the transgene will therefore be rendered male-sterile. No pollen grain carrying a transgene will therefore be released into the environment. If the plant is homozygous for the transgene, all the harvested seeds carry the gene and therefore express the phenotype.

Cultivating these plants with a view to production is performed by cultivating pollinating plants in the vicinity of the transgenic male-sterile plants. This can be achieved either by mixing seeds (10% of the pollinating plant seeds is sufficient) or by alternating female (male-sterile) lines and pollinating lines. In this latter case, only the females are harvested.

The invention also relates to a process for producing an expression product of a transgene of interest, characterized in that it comprises:

a) either transforming plant cells, in particular using a cell host as previously defined, which host is itself transformed with a vector which contains a transgene of interest combined with elements which enable it to be expressed in plant cells, which transgene is linked genetically to an AMS gene which is combined with elements which enable it to be expressed in plant cells, so as to integrate an AMS gene which is linked genetically to a transgene of interest into the genome of these cells;

or transforming plant cells which carry a cytoplasmic or nuclear male sterility so as to integrate a transgene of interest into the genome of these cells;

b) regenerating transformed plants from the abovementioned transformed plant cells;

c) recovering the expression product of the said transgene of interest in the said abovementioned transformed cells or plants, in particular by extraction followed, where appropriate, by a purification.

Another aspect linked to producing transgenic plants resides in the presence of genes which may possibly be judged to be undesirable, if not harmful, to humans and/or the environment, in particular in the eyes of the public.

Thus, in order to obtain transgenic plants, it is necessary to pick out, from millions of cells, those which contain the modification to be introduced. In order to do this, use is made of so-called marker genes which usually confer resistances to antibiotics or to herbicides. These genes are sometimes regarded as being undesirable, and various strategies (cotransformation, use of recombinases, etc.) have been envisaged for attempting to remove them.

Thus, Patent Application WO 92 01370 discloses a method for producing a transgenic plant containing a gene of interest free of marker genes, which method uses a transposition system.

Furthermore, application WO 91 09957 discloses a site-specific recombination method in plant cells which uses a Cre/lox system for producing a deletion, an insertion or a reciprocal exchange of DNA segments. The method which is described is applicable to removing a marker gene. The applicant also mentions the use of this method for restoring fertility within the context of producing hybrid seeds by means of genetic engineering.

However, in the prior art, male sterility had not been used as a marker, as such, in screening procedures.

According to one embodiment of the invention, the AMS gene is able to serve as a positive marker for screening for plants which have integrated a transgene of interest, with individuals possessing the said AMS gene being selected.

The presence of this AMS gene can be detected, in particular, by molecular analyses using polymerase chain reactions (PCRs) and/or by Southern blot analyses, in accordance with customary techniques (Sambrook et al., 1989). Plants possessing male sterility can also quite simply be selected by observing the presence or absence of the development of pollen grains. The AMS gene which has been used as a positive marker can then be regarded as being undesirable and can be excised.

According to another embodiment of the invention, the AMS gene makes it possible to improve the method of eliminating an undesirable exogenous DNA fragment within the context of procedures for screening for plants which have been genetically transformed.

Thus, in order to be effective, the existing screening strategies, which are based on using a marker gene and which are such as described in the above-mentioned patent applications, for example, should function at a very high frequency. The cells or plants which have lost the marker gene are no longer selectable as compared with those from which they are derived. The screening is then based on molecular methods which are cumbersome and onerous.

The applicant has now discovered the value of using a gene which confers artificial male sterility (AMS gene) as a "suicide marker" or "negative marker" of an excision event, namely that only the individuals which have lost it will replicate. This makes it possible to use strategies for eliminating an undesirable exogenous DNA fragment which have low yields and therefore makes it possible to broaden the fields of investigation in this sphere.

In accordance with the invention, the AMS gene is linked genetically to an undesirable DNA fragment such that the said AMS gene and the said undesirable DNA fragment can be excised simultaneously.

The said undesirable exogenous DNA fragment can, in particular, be a marker gene, preferably a gene which confers resistance to an antibiotic.

In general, the systems for eliminating undesirable genes are based on two components: an excisable DNA fragment which contains the undesirable gene and an inducer of this excision.

According to one embodiment of the invention, a gene conferring artificial male sterility is introduced into the excisable fragment. The plants which have been transformed with this first component will therefore be male-sterile and will be maintained by back-crossing. The inducer, which is supplied by a crossing, will lead to elimination of the DNA fragment containing the AMS gene, thereby giving rise to the development of fruits which are derived from self-fertilization. These fruits contain individuals from which the AMS gene and the undesirable gene have been removed.

In practice, it is sufficient to collect the only seeds which are produced by means of self-fertilization by the F1 plants containing the two components.

According to another embodiment of the invention, the plant which has integrated the excisable DNA fragment containing the AMS gene can be transformed with a DNA fragment which induces the excision.

The excision system which is used in accordance with the invention for eliminating the undesirable DNA fragment can be a transposition system, such as, in particular, the maize Ac/Ds system, or a recombination system such as, in particular, the P1 bacteriophage Cre/lox system, the yeast FLP/FRT system, the Mu phage Gin recombinase, the *E. coli* Pin recombinase, or the pSR1 plasmid R/RS system.

An aim of the present invention is also to provide a vector, in particular a plasmid, which is characterized in that it contains an excisable DNA fragment which comprises an undesirable DNA fragment and the said AMS gene, with the said undesirable DNA fragment preferably being a marker gene, preferably a gene which confers resistance to an antibiotic, with the said AMS gene and the said undesirable DNA fragment each respectively being combined with elements which enable them to be expressed in plant cells, in particular a promoter and a transcription terminator.

The said vectors according to the invention are used for transforming plant cells.

The invention finally relates to a kit for implementing the process of eliminating an excisable fragment, characterized in that it contains, on the one hand, a vector as previously defined, which vector contains a transgene of interest which is combined with elements which enable it to be expressed in plant cells and which is linked genetically to an AMS gene which is combined with elements which enable it to be expressed in plant cells, comprising an excisable AMS gene, or a plant or plant part which has been transformed with the said vector, and, on the other hand, a vector which carries a source of transposase or recombinase, or a plant or plant part which has been transformed with the said vector.

DESCRIPTION OF THE PREFERRED EMBODIMENTS

Plant cells can be transformed by transferring the above-mentioned vectors into protoplasts, in particular after incubating these latter in a solution of polyethylene glycol (PG) in the presence of divalent cations ($Ca^{2+}$) in accordance with the method described in the article by Krens et al., 1982.

Plant cells can also be transformed by electroporation, in particular in accordance with the method described in the article by Fromm et al., 1986.

Plant cells can also be transformed by using a gene gun which enables metallic particles covered with the DNA sequences of interest to be projected at very high velocity, thereby delivering the genes to the interior of the cell nucleus, in particular in accordance with the technique described in the article by Sanford (1988).

Another method of transforming plant cells is that of cytoplasmic or nuclear microinjection.

According to a particularly preferred embodiment of the process of the invention, the plant cells are transformed with a vector according to the invention, with the said cell host being capable of infecting the said plant cells while enabling the DNA sequences of interest which were initially contained in the genome of the abovementioned vector to be integrated into the genome of these plant cells.

Advantageously, the abovementioned cell host which is employed is *Agrobacterium tumefaciens*, in particular in accordance with the methods described in the articles by Bevan, 1984, and An et al., 1986, or else *Agrobacterium rhizogenes*, in particular in accordance with the method described in the article by Jouanin et al., 1987.

Preferably, the plant cells are transformed by transferring the T region of the *Agrobacterium tumefaciens* Ti tumour-inducing extrachromosomal circular plasmid using a binary system (Watson et al.).

In order to do this, two vectors are constructed. In one of these vectors, the T-DNA region has been removed by deletion, apart from the left and right borders, with a marker gene being inserted between them to enable selection to take place in the plant cells. The other partner of the binary system is a helper Ti plasmid, i.e. a modified plasmid which no longer possesses T-DNA but still contains the vir virulence genes which are required for transforming the plant cell. This plasmid is maintained in Agrobacterium.

The AMS gene and the gene of interest can be combined together, or each respectively, with a transcriptional control system, in particular a promoter and a transcription terminator.

The AMS gene can, in particular, be combined with a transcriptional control system which comprises a promoter which permits specific expression in the anther, such as the A3 or A9 promoter (WO 92 11379) or the TA29, TA26 or TA13 promoters (WO 89 10396).

Transcription terminators which can be used and which may be mentioned are the cauliflower mosaic virus (CaMV) polyA 35S terminator, which is described in the article by Franck et al., (1980), or the polyA NOS terminator, which corresponds to the 3' non-coding region of the nopaline synthase gene of the *Agrobacterium tumefaciens* nopaline strain Ti plasmid (Depicker et al., 1982).

Transcription promoters which can be used, for example in combination with the gene of interest, and which may in particular be mentioned are:

the 35S promoter or, advantageously, the CaMV 35S double constitutive promoter (35Sdp), which are described in the article by Kay et al., 1987;

the PCRU promoter of the radish cruciferin gene, which enables the recombinant polypeptides of the invention to be expressed solely in the seeds (or grains) of the plant obtained from cells which have been transformed in accordance with the invention and which is described in the article by Depigny-This et al., 1992;

the PGEA1 and PGEA6 promoters which correspond to the 5' non-coding region of the *Arabidopsis thaliana* seed storage protein genes GEA1 and GEA6, respectively (Gaubier et al., 1993), and which permit specific expression in seeds;

the SPP superpromoter chimeric promoter (Ni M et al., 1995), which consists of the fusion of a triple repeat of a transcriptional activator element of the promoter of the *Agrobacterium tumefaciens* octopine synthase gene, of a transcriptional activator element of the promoter of the mannopine synthase gene and of the *Agrobacterium tumefaciens* mannopine synthase promoter;

the rice actin promoter followed by the rice actin intron (RAP-RAI) contained in the pAct1-F4 plasmid described by McElroy et al., 1991;

the barley HMWG (high molecular weight glutenine) promoter (Anderson O. D. et al., 1989);

the promoter of the maize γzein gene (Pγzein), which is contained in the plasmid pγ63 described in Reina et al., 1990, and which permits expression in the albumen of maize seeds.

Advantageously, the gene for male sterility and the gene of interest are combined with one or more sequences encoding a peptide which is responsible for directing the recombinant polypeptides into a predetermined compartment of the plant cell, in particular into the endoplasmic reticulum or into the vacuoles, or even to the exterior of the cell, into the pectocellulose wall or into the extracellular space which is also termed the apoplasm.

These sequences which encode a directing peptide can be of plant, human or animal origin.

Sequences which encode a directing peptide of plant origin and which may be mentioned are:

the nucleotide sequence of 69 nucleotides (indicated in the examples below) which encodes the 23 amino acid prepeptide (signal peptide) of sporamine A in the sweet potato, with this signal peptide enabling the recombinant polypeptides of the invention to enter the secretory system of the plant cells which have been transformed in accordance with the invention (namely the endoplasmic reticulum in the main);

the nucleotide sequence of 42 nucleotides (indicated in the examples below) which encodes the 14 amino acid, vacuole-directing N-terminal propeptide of sporamine A in sweet potato and which enables the recombinant polypeptides of the invention to accumulate in the vacuoles of the plant cells which have been transformed in accordance with the invention;

the nucleotide sequence of 111 nucleotides (indicated in the examples below) which encodes the 37 amino acid prepropeptide of sporamine A, consisting of the N-terminal part to the C-terminal part of the 23 amino acids of the abovementioned signal peptide followed by the 14 amino acids of the above-mentioned propeptide, with this prepropeptide enabling the recombinant polypeptides of the invention to enter the secretory system, and to accumulate in the vacuoles, of the plant cells which have been transformed in accordance with the invention;

with the abovementioned three sequences being described in the articles by Murakami et al., 1986 and Matsuoka et al., 1991;

the carboxyterminal propeptide of barley lectin, which is described, in particular, in the articles by Schroeder et al., 1993, and Bednarek et al., 1991;

and the PRS (pathogenesis-related protein, Cornelissen et al., 1986) which permits secretion.

One of the sequences encoding a directing peptide which may also be mentioned is that which encodes the peptides KDEL, SEKDEL and HDEL at the C-terminal end and which directs into the endoplasmic reticulum.

Plant cells which are capable of being transformed in accordance with the present invention and which may be mentioned are those of rape, tobacco, maize, pea, tomato, carrot, wheat, barley, potato, soybean, sunflower, lettuce, rice and lucerne.

The genes of interest which are to be integrated into the genome of the plant cell can, in particular, be genes which encode proteins which are of human or animal origin and which can be of therapeutic or prophylactic interest, such as collagen, gastric lipase, etc.

The marker genes employed can, in particular, be genes which confer resistance to antibiotics such as hygromycin, kanamycin, bleomycin or streptomycin, or to herbicides such as glufosinate, glyphosate or bromoxynil.

EXAMPLES

The various plasmids are constructed and ligated, and *Escherichia coli* DH5α bacteria which have previously been rendered competent are transformed, using the customary recombinant DNA techniques (Sambrook et al., 1989).

Example 1

Construction of a Binary Plasmid which Combines Male Sterility which is Conferred by the Gene Encoding PR Glucanase, Production of Gog Gastric Lipase, Selection on Kanamycin and Selection on Basta, and which can be used in Rape Transgenesis.

The "binary" plasmid derivative of pGA492 (An, 1986), which contains the following sequences on its transfer DNA between the right and left borders originating from the *Agrobacterium tumefaciens* pTiT37 plasmid: the constitutive promoter of the nos gene encoding nopaline synthase (Depicker et al., 1982), the sequence encoding the NPTII gene, which encodes neomycin phosphotransferase which confers resistance to kanamycin (Berg and Berg, 1983), which sequence has been deleted for the region of the first 8 codons, including the methionine ATG start codon, and fused to the sequence of the first 14 codons of the sequence encoding the nos gene (Depicker et al., 1982), the sequence which encodes the nos gene but which lacks the region of the first 14 codons, the nos terminator (Depicker et al., 1982), a region which contains multiple cloning sites (also termed a polylinker) (HindIII-XbaI-SacI-HpaI-KpnI-ClaI-BglII) and which precedes the CAT gene, which encodes chloramphenicol acetyltransferase (Close and Rodriguez, 1982), and the terminator sequences of gene 6 of the *Agrobacterium tumefaciens* pTiA6 plasmid (Liu et al., 1993).

a) Construction of the Plasmid pBIOC500 Carrying the Gene Conferring Male Sterility.

The chimeric gene which corresponds to the "A9PR-glucanase-T35S promoter", contained in pDW80PR (Worall et al., 1992), was used. The KpnI/EcoRV fragment carrying this chimeric gene was isolated by means of a double enzyme digestion with KpnI and EcoRV, purified by electroelution following electrophoretic migration on an 0.8% agarose gel, precipitated with alcohol and then dried. It was inserted in the KpnI and SmaI sites of the pBluescript KS+ plasmid marketed by Stratagene. The ligation was carried out at 14° C. for 16 hours using 100 ng of the dephosphorylated plasmid and 50 ng of KpnI/EcoRV fragments in a 10 µl reaction medium in the presence of 1 µl of 10×T4 DNA ligase buffer (Amersham) and 2.5 U of T4 DNA ligase enzyme (Amersham). *Escherichia coli* DH5α bacteria, which had previously been rendered competent, were transformed. The plasmid DNA harboured by the resulting clones, which were selected on a medium containing 50 µg of ampicillin/ml, was extracted by the alkaline lysis method and analysed by enzyme digestion with restriction enzymes. The KpnI/SstI fragment from the resulting plasmid, which fragment carried the above-described chimeric gene, was introduced between the KpnI and SstI sites of pGA492. The chimeric fragment was isolated by the customary methods. The ligation was carried out at 14° C. for 16 hours using 100 ng of the dephosphorylated vector and 50 ng of fragments carrying the KpnI/SstI fragment in a 10 ml reaction medium in the presence of 1 µl of 10×T4 DNA ligase buffer (Amersham) and 2.5 U of T4 DNA ligase enzyme (Amersham). *Escherichia coli* DH5α bacteria, which had previously been rendered competent, were transformed. The plasmid DNA harboured by the resulting clones, which were selected on medium containing 12 µg of tetracycline/ml, was extracted by the alkaline lysis method and analysed by enzyme digestion with restriction enzymes. The resulting vector is termed pBIOC500.

b) Construction of the Plasmid pBIOC501 Carrying the Gene Conferring Resistance to Basta.

The EcoRI/HindIII fragment carrying the chimeric "P35S-pat-TNOS" gene, which was isolated from the plasmid pIB16.1 (Broer et al., 1988), was inserted between the EcoRI and HindIII sites of pBSIISK+, which was marketed by Stratagene and which was modified by adding a KpnI site into the SmaI site of the pBSIISK+ polylinker sequence. The resulting plasmid is termed pBIOC501. The plasmid DNA harboured by the resulting clones, which were selected on medium containing 50 µg of ampicillin/ml, was extracted by the alkaline lysis method and analysed by enzyme digestion using restriction enzymes.

c) Construction of the Plasmid pBIOC502 Carrying the Gene Encoding Dog Gastric Lipase.

The chimeric gene corresponding to "PCRU-PSLGL-LGC-T35S", which was isolated from pBIOC93, which is described in application WO 9633277, is carried by the fragment which is obtained by double digestion with SacI and XhoI, with the SacI site being repaired by the action of the enzyme T4 DNA polymerase (New England Biolabs) in accordance with the manufacturer's recommendations. This fragment was inserted between the ApaI site, which was treated with the enzyme T4 DNA Polymerase, and the XhoI site of plasmid pBIOC501. The resulting plasmid is termed pBIOC502. The plasmid DNA harboured by the resulting clones, which were selected on medium containing 50 µg of ampicillin/ml, was extracted by the alkaline lysis method and analysed by enzyme digestion using restriction enzymes.

d) Construction of the Binary Vector pBIOC503.

A KpnI fragment carrying the "PCRU-PSLGL-LGC-T35S" and "P35S-pat-TNOS" expression cassettes was isolated from pBIOC502 and ligated into the KpnI site of pBIOC500. The resulting plasmid is termed pBIOC503. The plasmid DNA harboured by the resulting clones, which were selected on medium containing 12 µg of ampicillin/ml, was extracted by the alkaline lysis method and analysed by enzyme digestion using restriction enzymes.

The plasmid DNA of plasmid pBIOC503 was introduced by direct transformation into the *Agrobacterium tumefaciens* strain LBA4404 in accordance with the method of Holsters et al. (1978).

Example 2

Construction of a Binary Plasmid which Combines Male Sterility Conferred by the Gene Encoding Barnase, Production of Dog Gastric Lipase, Selection on Kanamycin and Selection on Basta, and which can be Used in Rape Transgenesis.

a) Construction of the Plasmid pBIOC504 Carrying the Gene Conferring Male Sterility.

The chimeric gene which corresponds to the "A9-barnase-T35S promoter", which is contained in pWP173 (Paul et al., 1992), was used. The KpnI/EcoRV fragment carrying this chimeric gene was inserted at the KpnI and SmaI sites of the pBluescript KS+ plasmid which is marketed by Stratagene. The KpnI/SstI fragment carrying the above-described chimeric gene was obtained from the resulting plasmid and introduced at the KpnI and SstI sites of pGA492. The resulting vector is termed pBIOC504. The plasmid DNA harboured by the resulting clones, which were selected on medium containing 50 µg of ampicillin/ml, was extracted by the method of alkaline lysis and analysed by enzyme digestion using restriction enzymes.

b) Construction of the Plasmid pBIOC501 Carrying the Gene Conferring Resistance to Basta.

The vector was constructed as described in Example 1b).

c) Construction of the Plasmid pBIOC502 Carrying the Gene Encoding Dog Gastric Lipase.

The vector pBIOC502 was constructed as described in Example 1c).

d) Construction of the Vector pBIOC505.

A KpnI fragment carrying the "PCRU-PSLGL-LGC-T35S" and "P35S-pat-TNOS" expression cassettes was isolated from pBIOC502 and ligated into the KpnI site of pBIOC504. The resulting plasmid is termed pBIOC505. The plasmid DNA harboured by the resulting clones, which were selected on medium containing 50 µg of ampicillin/ml, was extracted by the alkaline lysis method and analysed by enzyme digestion using restriction enzymes.

The plasmid DNA of plasmid pBIOC505 was introduced by direct transformation into the *Agrobacterium tumefaciens* strain LBA4404 in accordance with the method of Holsters et al. (1978).

Example 3

Obtaining Trangenic Rape Plants

Spring rape (*Brassica napus* cv WESTAR or Limagrain lines) seeds are disinfected for 40 minutes in a 15% Domestos solution. After four rinses with sterile water, the seeds are set, at the rate of 20 seeds per pot of 7 cm in diameter and 10 cm in height, to germinate on Murashige and Skoog mineral medium (Sigma M 5519) which contains 30 g of sucrose/l and which is solidified with 5 g of agar gel/l. These pots are placed in a 26° C. culture chamber with a photoperiod of 16H/8H and under a luminous intensity of the order of 80 $\mu E.m^{-2}.S^{-1}$.

After five days of germination, the cotyledons are collected in a sterile manner by cutting each petiole approximately 1 mm above the cotyledon node.

In parallel, *Agrobacterium tumefaciens* strain LBA4404, which harbours the binary plasmids, is precultured at 28° C. for 36 hours in 10 ml of 2YT bacterial medium (Sambrook et al., 1989), which is supplemented with the antibiotics which can be used for selecting the strain employed, in a 50 ml Erlenmeyer flask.

This preculture is used, at a 1% concentration, to seed a new bacterial culture which is carried out under the same conditions. After 14 hours, the culture is centrifuged at 3000 g for 15 minutes and the bacteria are taken up in an equivalent volume of liquid germination medium. This suspension is aliquoted into 5 cm diameter Petri dishes at the rate of 5 ml/dish.

The severed end of the petiole is immersed for a few seconds in the agrobacteria solution which has thus been prepared, after which the petiole is thrust a few millimeters into the regeneration medium. This medium has the same basal composition as the germination medium except that, in addition, it contains 4 mg of benzylaminopurine (BAP)/l, which is a phytohormone which promotes the new formation of buds. Ten explants (cotyledon with petiole) are cultured in 9 cm diameter Petri dishes (Greiner, cat. No. 664102).

After two days of coculture under the same environmental conditions as in the germinations, the explants are transplanted into phytatray dishes (Sigma, cat. No. P1552), which contain the previous medium supplemented with a selective agent: 45 mg of kanamycin sulphate/l (Sigma, cat. No. K 4000) and a bacteriostatic agent: mixture of 1/6 by weight of clavulanic acid potassium salt and 5/6 by weight of amoxicillin sodium salt (Augmentin® injectable) at the rate of 600 mg/l.

Twice in succession, at an interval of three weeks, the explants are transplanted, under sterile conditions, onto new medium under the same conditions.

The green buds which have appeared at the end of the second or third transplantation are separated from the explant and cultured individually in transparent pots of 5 cm in diameter and 10 cm in height which contain a medium which is identical to the previous one but lacks BAP. After three weeks of culture, the stalk of the transformed bud is severed and the bud is transplanted into a new pot of fresh medium. At the end of three to four weeks, the roots are sufficiently developed to enable the plantlet to be acclimatized in a phytotron. The buds which are not green or rooted are removed. These plantlets are then transplanted into 7 cm-sided pots which are filled with water-saturated compost (NF U44551 standard: 40% brown peat, 30% sifted heath soil and 30% sand). After two weeks of acclimatization in a phytotron (temperature: 21° C.; photoperiod: 16H/8H and 84% relative humidity), the plantlets are repotted into 12 cm diameter pots which are filled with the same compost which is enriched with a slow-release fertilizer (Osmocote, at the rate of 4 g/l of compost) and then moved into a greenhouse (class S2), with the temperature being set at 18° C. and with the plantlet being watered twice daily for two minutes on each occasion.

As soon as the flowers have appeared, they are bagged (Crispac, cat. No. SM 570y 300 mm*700 mm) so as to prevent cross-fertilization.

When the siliques have reached maturity, they are harvested, dried and then threshed. The seeds which are obtained are used for assaying the biochemical activity of the gene of interest.

The transgenic progeny is selected by germinating on a medium containing kanamycin sulphate at the rate of 100 to 150 mg/l (depending on the genotypes). The procedural conditions are identical to those described above apart from the fact that the germinations are carried out in glass tubes using one single seed per tube. Only plantlets which develop secondary roots during the first three weeks are acclimatized in a phytotron before being transferred to a greenhouse.

Example 4

Obtaining Transgenic Tobacco Plants

The tobacco plants which are used for the transformation experiments (*Nicotiana tabacum* var. *Xanthi* NC and PBD6) are cultured in vitro on a basal Murashige and Skoog (1962) medium which additionally contains Gamborg et al (1968) vitamins (Sigma cat. No. M0404), 20 g of sucrose/l and 8 g of agar (Merck)/l. The pH of the medium is adjusted to 5.8 with potassium hydroxide solution before autoclaving at 120° C. for 20 minutes. The tobacco plantlets are transplanted every 30 days, by means of internode cuttings, onto this MS20 propagation medium.

All the in vitro cultures are carried out in an air-conditioned enclosure under the conditions defined below:

luminous intensity of 30 $\mu E.m^{-2}.S^{-1}$, photoperiod of 16 hours;

thermoperiod of 26° C. during the day and 24° C. during the night.

The transformation technique employed is derived from that of Horsch et al. (1985).

*Agrobacterium tumefaciens* strain LBA4404, which harbours the binary plasmids, is precultured at 28° C. for 48 hours, with shaking, in LB medium (Sambrook et al., 1989) which additionally contains appropriate antibiotics (kanamycin). The preculture is then diluted 1/50 in the same medium and cultured under the same conditions. After having been incubated overnight, the culture is centrifuged (3000 g, 10 minutes) and the bacteria are taken up in an equivalent volume of liquid MS30 medium (30 g of sucrose/l), and this suspension is diluted 1/10.

Explants of approximately 1 cm² in size are cut out from the leaves of the above-described plantlets. They are then placed in contact with the bacterial suspension for one hour, after which they are rapidly dried on filter paper and placed on coculture medium (solid MS30).

After two days, the explants are transferred onto MS30 regeneration medium in Petri dishes, with this medium containing a selective agent, i.e. kanamycin (2000 mg/l), a bacteriostatic agent, i.e. Augmentin® (400 mg/l), and the hormones which are required for inducing buds (1 mg of BAP/l and 0.1 mg of ANA/l). After two weeks of culture, the explants are transplanted onto the same medium. After two further weeks, the buds are transplanted onto development medium composed of MS20 medium, which additionally contains kanamycin and Augmentin, in Petri dishes. After fifteen days, half the buds are transplanted. Rooting takes approximately 20 days, at the end of which the plantlets can be cloned by means of internode cuttings or taken out into a greenhouse.

Example 5

Construction of a Source of Transposase.

A binary plasmid was constructed which carried a source of fixed transposase under the 35S promoter since the latter proved to lead to strong and early expression of this transposase (Finnegan et al., 1993).

In order to do this, the BamHI/EcoRI fragment of pBI35S Ac (constructed by Finnegan) was cloned at the BamHI and SnaBI sites of pBI121 (Jefferson et al., 1987). The resulting plasmid, termed pBIOS144, contains, between the left and right borders, the gene for resistance to kanamycin, i.e. NPTII, under the nos promoter and terminator. The Ac element whose 5' part has been deleted and which is under the 35S promoter and which thus constitutes the source of fixed transposase, and 1400 base pairs of the 5' part of the gene encoding E. coli β-glucuronidase (GUS gene, marked del GUS in FIG. 3), and, finally, the nos terminator.

Example 6

Construction of the Ds:Kana$^R$-AMS Element.

The successive steps which led to the construction of this vector are as follows:

a) Construction of the Plasmid pBIOC203 Carrying the Gene Conferring Resistance to Kanamycin.

The 1 Kb BamHI fragment (corresponding to the NPTII gene) of pCamVNEO (Fromm et al., 1986) was inserted into the BamHI site of pBIOS1 (Perez et al., 1989). The resulting vector pBIOS 1K was digested with EcoRI. The EcoRI fragment from BIOS 1K was then blunt-ended with Klenow polymerase and then cloned into the plasmid AF 3'Ac (Cocherel et al., 1996) at the EcoRI site, thus giving rise to pBIOS203.

b) Construction of the Plasmid pBIOS208 Carrying the AMS Gene.

The EcoRI fragment from the vector pEGS phleo, containing 399 base pairs from the 5' end of the Ac element (Cocherel et al., 1996) was cloned into pBSsk (Stratagene) at the EcoRI site, thereby giving rise to pBIOS204.

The EcoRI/HindIII fragment (comprising the 3' end of Ac and the NPTII cassette) from pBIOS203 was cloned into pBSsk at the EcoRI-HindIII sites, thereby giving rise to pBIOS205.

The SmaI fragment from pBIOS204 (comprising the 5' end of Ac) was cloned into the SmaI site of pBIOS205, thereby giving rise to pBIOS206.

The SphI fragment from DW 80 bin PR-glucanase, containing the PR-glucanase (PR-Glu) gene under the A9 promoter and CaMV terminator (Worall et al., 1992), was cloned into the EcoRI site of pBIOS206. In the resulting plasmid, i.e. pBIOS208, the A9-PR-glucanase gene is inserted in the opposite orientation to the NPTII gene.

c) Insertion of the Ds::Kana$^R$-AMS Element into a Binary Vector.

The vector pGA 492DL was obtained after the following modifications had been made to pGA 492 (G. An):

deletion of the SacII/ClaI fragment corresponding to the cassette for expressing the chimeric NPTII gene. This new vector is termed pGa 492D;

replacement of the BglII/ScaI fragment (loss of a part of the CAT gene) of pGA 492D with the SacI/KpnI polylinker from pBSIIsk. This new vector is termed pGA 492 DL.

The HindIII/SpeI fragment from pBIOS208 was cloned at the HindIII/SpeI sites of pGA 492 DL in order to create the binary plasmid pBIOS232. The structure of this T-DNA is shown diagrammatically in FIGS. 1 and 2.

Example 7

Transformation and Selection of Tomato a) Transformation of Tomato (UC82B Variety) with the Constructed Binary Vector.

The binary vector pBIOS232 was transferred into the *Agrobacterium* strain LBA 4404 by means of triparental conjugation in accordance with the technique described by Ditta et al.

Tomato was transformed in accordance with the modified technique of J. Fillatti:

Seeds of the cultivar UC82B are sterilized for 15 minutes in 10% Domestos and rinsed three times in sterile water.

They are then sown in pots containing MSSV/2 culture medium for seven or eight days.

The cotyledons are removed and cut transversely into three parts. Only the central part is retained, with this part being cultured, at 26° C. and in the light, on KCMS medium containing added Acetosyringone, with the lower surface against the medium.

*Agrobacterium* strain LBA 4404 bacteria are cultured overnight in LB medium which is supplemented with the appropriate selective agent (tetracycline). On the following day, the culture is centrifuged and the resulting pellet is taken up in liquid KCMS medium.

The explants are soaked for approximately 30 minutes in an *Agrobacterium* solution which has been diluted 1/20 in KCMS medium containing added Acetosyringone. They are then dried rapidly on filter paper.

The explants are then:

replaced on the same KCMS medium for two days, in the dark and at 26° C.;

washed in liquid 2Z medium containing added Augmentin (400 mg/l) and dried on filter paper;

transferred onto solid 2Z medium containing 400 mg of Augmentin/l and 100 mg of kanamycin/l; cultured in the light at 26° C.; and transplanted onto fresh 2Z medium a fortnight later.

The first buds appear three weeks after the coculture. When they reach a size of approximately 1 cm, they are separated from the explant and transplanted onto Dev medium where they root within one or two weeks if they have been properly transformed.

When they are well rooted, they are transplanted into Jiffy-7 earth (from AS Jiffy Products) in a phytotron, where they acclimatize rapidly.

As soon as the root system is well developed in "Jiffy", the plants are transplanted into 12 cm diameter pots and then into 30 cm diameter containers and cultured in a greenhouse while being watered automatically with a nutritive solution (a diluted 5 kg/50 l solution which is supplied at 1.6%).

b) Molecular Analysis of the Primary Transformants Containing pBIOS144 or pBIOS232 T-DNA.

When the transformed plants have developed sufficiently in the greenhouse, leaves (approximately 5 g) are removed for the DNA to be extracted from them, with this DNA then being analysed by Southern blotting in accordance with currently employed methods (Sambrook et al.).

The DNA from each plant is digested with the enzyme HindIII. After migration and transfer onto a nitrocellulose membrane, the DNA samples are hybridized with a variety of probes which make it possible to verify:

the number of T-DNA copies which were inserted,
whether the whole of the T-DNA was inserted,
the presence or absence of sequences external to the borders.

After these molecular analyses have been completed, only those plants are selected which contain a single intact T-DNA without any sequences external to the borders.

The same protocol was implemented for transforming tomato cells with plasmid pBIOS144 and selecting the transformed plants.

Example 8

Assessing the Source of Fixed Transposase

Once the source of fixed transposase has been integrated into the plants, tests are carried out to check that it is able to activate a "Ds" element. To do this, the selected plants harbouring the pBIOS144 plasmid are crossed with a plant which contains a tester Ds element whose excision restores the activity of the Gus (β-glucuronidase) gene. This Ds was constructed in two steps:

the BglII/SpeI fragment from pBIOS206, corresponding to Ds::Kana$^R$, was inserted at the BamHI/XbaI sites of pBI221 (Clontech) in order to obtain pBIOS226.

The entire pBIOS226 plasmid was then inserted into the HindIII site in pGA 492 DL. The resulting binary plasmid, i.e. pBIOS228, contains, between the right and left borders, the Ds::Kana$^R$ between the 35S promoter and the coding part of the Gus gene.

Any excision of this Ds::Kana$^R$ will be evidenced by expression of the Gus reporter gene. A Gus test (Jefferson et al.) is carried out on the F1 progeny of this type of cross in order to assess the efficacy of the various lines containing the transposase. Blue spots were detected on cotyledons and areas on the leaves of plants which were derived from a cross between a "transposase" line and a "Ds tester" line. The number of spots and areas on a plant attests to the efficacy of the transposase source in this plant.

Example 9

Generation of Lines of Fixed Transposase

The single-copy transformants lacking sequences external to the borders which were selected and assessed to be positive as described in the preceding example were subjected to two consecutive cycles of self-fertilization. The batches of T2 seeds were harvested separately.

The segregation for resistance to kanamycin was assessed in the case of each T2 in order to detect the batches of homozygous seeds. Some thirty seeds from each batch are sown in soil in a greenhouse. Eighteen days after the sowing, a 400 mg/l solution of kanamycin is sprayed onto the plantlets for a period of three days (Weide et al.). Five days later, it is readily possible to identify the plants which are sensitive to kanamycin. The batches of plants which are homozygous for the transgene are identified in accordance with the segregation of the resistant and sensitive plants and in conformity with the Mendelian segregation of a dominant gene. These batches are those which are preferentially retained and which will be used for crossing the plants which contain the Ds::Kana$^R$-AMS element.

Example 10

Crossing the Ds::Kana$^R$-AMS Lines with Homozygous "Transposase" Lines

The primary transformants which have been selected (single-copy and without any sequences external to the borders) are assessed, as soon as they have flowered in the greenhouse, for fertility by examining transverse sections, which are stained with carmine acetic acid, of the anther tube of one or two flowers per plant under the microscope. At the conclusion of this assessment, only those male-sterile plants which do not exhibit any pollen are retained.

The sterile plants carrying the Ds::Kana$^R$-AMS are fertilized with pollen from lines expressing the Ac transposase. The fruits are harvested and the seeds are removed.

Example 11

A—Identification of an Excision Event in the F1 Plants

Figure 1:
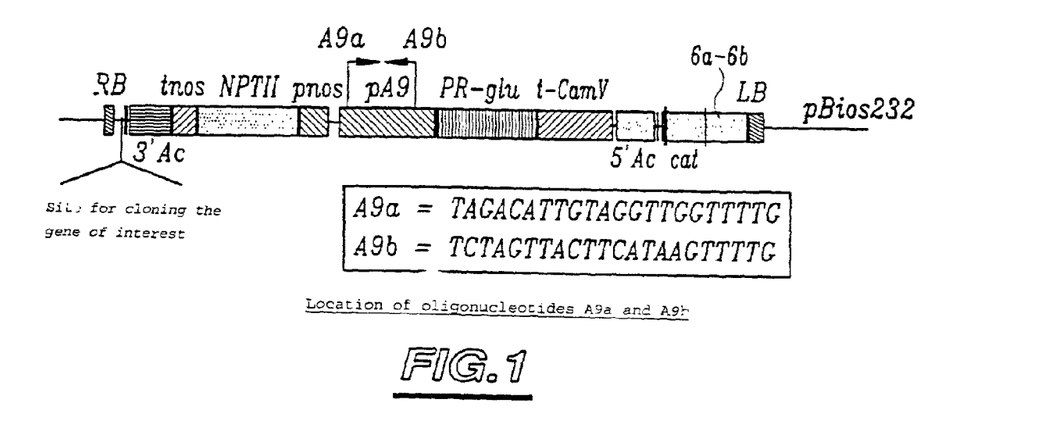
FIG. 1 shows the location of oligonucleotides A9a (SEQ ID NO: 4) and A9b (SEQ ID NO: 5) used in Example 11.

The seeds derived from the crossing between the plants carrying the transposase source and those carrying the Ds::Kana$^R$-AMS are sown in compost in a greenhouse. At the cotyledon stage, one cotyledon per plantlet is removed with a view to extracting the DNA rapidly (Lassner et al., 1989) for the purpose of carrying out a PCR test using the oligonucleotides A9a and A9b (FIG. 1). The PCR conditions employed are as follows:

DNA: 40 ng (or 10 μl of the microextraction)
oligo A9a (10 pmol/μl): 3 μl
oligo A9b (10 pmol/μl): 3 μl
10× buffer: 10 μl
DNTP mix (5 mM): 4 μl
Promega Taq: 0.4 μl
25 mM MgCl$_2$: 8 μl
H$_2$O qs for 100 μl The reactions are carried out in a Perkin 9600 appliance.

After 2 minutes of denaturation at 95° C., 40 cycles of the following procedures are carried out:

30" of denaturation at 94° C.
30" of hybridization at 55° C.
1'30" of elongation at 72° C.

The aim of this test is to identify rapidly the plants which are carrying the AMS gene (800 base pair band in the PCR) as compared with those which are not carrying it (no band in the PCR). The plants which are carrying the AMS gene are repotted and, during their flowering, the appearance of fruits which might display one or more areas of somatic excision is monitored. The examination of fruits on F1 plants shows either an excision without reinsertion of the Ds or an excision followed by a reinsertion with loss of activity.

In order to verify this, the seeds derived from these fruits are removed and sown. A PCR molecular analysis of these plants is carried out in order to verify that they no longer carry the Ds::Kana$^R$-AMS but that they possess the "scar" of the T-DNA and/or the gene of interest. In order to do this, one cotyledon is removed from each plantlet for rapid extraction of the DNA.

Figure 2:
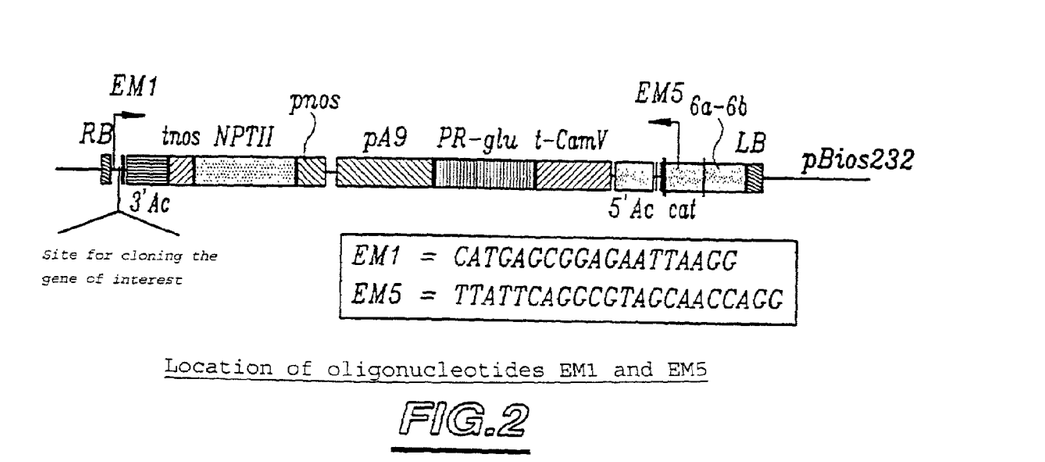
FIG. 2 shows the location of oligonucleotides EM1 (SEQ ID NO: 6) and EM5 (SEQ ID NO: 7) used in Example 11.

An aliquot of this DNA is removed in order to be subjected to two PCR reactions:

one reaction using the oligonucleotides EM1 and EM5 (FIG. 2),

The PCR conditions employed are as follows:
DNA: 40 ng (or 10 µl of the microextraction)
oligo EM1 (10 pmol/µl): 3 µl
oligo EM5 (10 pmol/µl): 3 µl
10× buffer: 10 µl
dNTP mix (5 mM): 4 µl
Promega Taq: 0.4 µl
25 mM MgCl$_2$: 18 µl
BSA: 8 µl
Glycerol: 2.5 µl
H$_2$O qs for 100 µl The reactions are carried out in a Perkin 9600 appliance.

After 2 minutes of denaturation at 95° C., 40 cycles of the following procedures are carried out:
30" of denaturation at 94° C.
30" of hybridization at 62° C.
45" of elongation at 72° C.

Figure 3:
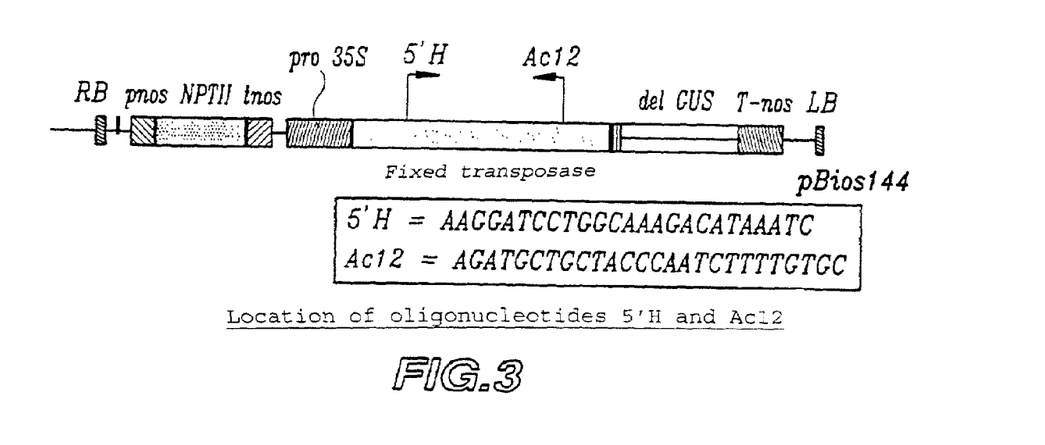
FIG. 3 shows the location of oligonucleotides 5'H (SEQ ID NO: 8) and Ac12 (SEQ ID NO: 9) used in Example 11.

This test makes it possible to see whether the plantlet is carrying the scar of the T-DNA and/or the gene of interest. When the Ds element has been excised, a fragment is expected which is of approximately 300 base pairs in size, in the case of the scar alone, to which has to be added the size of the gene of interest;

and the other reaction using the oligonucleotides 5'H and Ac12 (FIG. 3).

The PCR conditions employed are as follows:
DNA: 40 ng (or 10 µl of the microextraction)
oligo 5'H (10 pmol/µl): 3 µl
oligo Ac12 (10 pmol/µl): 3 µl
10× buffer: 10 µl
DNTP mix (5 mM): 4 µl
Promega Taq: 0.4 µl
25 mM MgCl$_2$: 18 µl
100× BSA: 8 µl
Glycerol: 2.5 µl
H$_2$O qs for 100 µl The reactions are carried out in a Perkin 9600 appliance.

After 2 minutes of denaturation at 95° C., 40 cycles of the following procedures are carried out:
30" of denaturation at 94° C.
30" of hybridization at 62° C.
1'30" of elongation at 72° C.

This test enables the absence of the gene encoding the transposase to be verified. If there is no amplified fragment, the transposase is absent. If the transposase is present, a 1.6 kb band is detected.

The plants which are derived from excision events and which now only carry the gene of interest, without the resistance to kanamycin or the T-DNA carrying the gene encoding the transposase will be positive with the first set of oligonucleotides (EM1–EM5) and negative with the second set (5'H-Ac12).

A Southern analysis carried out on these plants enables the presence of the gene of interest, and the absence of the gene for resistance to kanamycin, to be confirmed.

B—Identification of Transformants Which Lack the Selective Marker

1) Materials

NPTII Probe:

Amplification of a 1 kb fragment of the NPTII gene of the vector pBIOS232 using the oligonucleotides Kana7 and Kana8, which have the following sequences:

Kana 7: gctcgacgttgtcactgaag
Kana 8: cccggaaaacgattccgaag

The NPTII gene employed was isolated from the *Escherichia coli* transposon Tn5 (Berg and Berg, 1983).

Cat intra LB +intra RB Probes:

Mixture of 2 probes:

Cat int LB: SalI fragment of the T-DNA of pGA 492 DL containing the left border and a part of the Cat gene Int RB; SalI fragment of the T-DNA of pGA 492 containing the right border.

The 2 probes taken together correspond to the whole of the T-DNA of pGA 492 DL, which is the basic vector which was used for constructing pBios 232, which was in turn used for creating the Ds::Kana$^R$-AMS plants.

2) Identification and Culture of Plants Containing Two Active Components:

F1 seeds derived from the crossing between a plant carrying Ds::Kana$^R$-AMS and a plant carrying the source of fixed transposase were obtained and sown. A PCR test was carried out on the DNA from the cotyledons of 173 plants using the oligonucleotides EM1 and EM5 as described above. This test identified 18 plants in which a 350 bp band was amplified by EM1–EM5, thereby revealing somatic excision events testifying to the presence and functional capability of the 2 elements of the system.

The system was developed using a T-DNA carrying a Ds::Kana$^R$-AMS but not the gene of interest. Because of this, the excision band which is revealed by an amplification carried out using EM1 and EM5 is approximately 350 bp in size. When a gene of interest has been inserted, the length of this band will be extended by the size of this gene. According to another embodiment, it is also possible to use oligonucleotides which are specific for the gene of interest.

These 18 plants were cultivated in a field for 4 months. The flowers were examined regularly in order to check the fertility of the anthers, and the appearance of fruits was also checked. In 3 out of these 18 plants, fruits only appeared on some clusters only. These plants were therefore chimeric for the male-sterile/male-fertile phenotypes. The fruits on these plants were harvested, cluster by cluster, while noting the hierarchy of the cluster in relation to the plant as a whole.

Seeds from fruits which had appeared on 3 clusters from the 3 plants which had once again become partially fertile were sown. Leaves from the resulting plantlets (4 plantlets/cluster) were removed for the purpose of extracting their DNA for a Southern-type analysis. The DNA was digested with the enzyme HindIII (unique site in the T-DNA) before being subjected to electrophoresis and transfer to a membrane. The 36 samples corresponding to the F2 progeny were treated at the same time as the DNA of the parents of the hybrid (the plant carrying the Ds::Kana$^R$-AMS and the plant carrying the source of fixed transposase) so as to have reference profiles. The Southern blot hybridization using the NPTII and Cat-int LB probes identified plants which no longer carried the T-DNA containing the transposase source nor the Ds::Kana$^R$-AMS but which did indeed contain the T-DNA scar by means of comparing with the profile of the parents.

We analysed 36 plants in all, without any prior selection with kanamycin, which plants derived from 3 clusters from the 3 plants in which fruits were observed.

3) Results of the Analysis:

20 plants carrying the "scarred" T-DNA, that is showing 1 band which hybridizes with the Cat int LB-RB probe and which is of a size which is less than that which is present in the parent carrying the Ds. This same band is not hybridized with the NPTII probe.

31 plants carrying the transposase source, that is showing a band which hybridizes with the NPTII probe and which is of a size which is identical to that which is revealed by the same probe in the parent carrying the source of fixed transposase.

5 plants carrying the empty T-DNA but not carrying the transposase source.

Out of 36 plants analysed, 5 were found to be appropriate transformants which now only carry the T-DNA carrying the gene of interest and which had excised the selection marker gene.

It is therefore possible to select appropriate transformed plants 2 generations after the primary transformant.

This technique has a large number of advantages. It makes it possible to identify transformants lacking the selective marker at an early stage.

The crossing of the primary transformant with the transposase source is facilitated and more reliable since the latter is male-sterile.

Finally, this technique makes it possible to screen a low number of plantlets in order to identify appropriate transformants: without any prior preselection, and after having analysed 36 progeny from 3 plants, 5 plants were identified which contained the T-DNA lacking the Ds::$Kana^R$-AMS.

Furthermore, it is possible to improve the identification of the transformants which lack markers:

if the progeny of the fruits which are produced on a plant carrying the Ds::$Kana^R$-AMS and the transposase source are treated prior to the Kanamycin, a quarter of plants should be $Kana^S$ instead of 15/16 (which is normally obtained if there was no Ds excision). Of these, ¾ are carriers of "appropriate" T-DNA, with the other quarter corresponding to classical segregants which do not carry any transgene. The observation of a segregation of ¾ resistant plants to ¼ sensitive plants furthermore makes it possible rapidly to confirm that the elimination system was effective.

It is therefore possible to identify appropriate progeny by analysing very few plants out of the F2 plantlets which are sensitive to kanamycin.

4) Conclusion:

This study shows that adding a gene conferring artificial male-sterility to the system for eliminating a marker gene by means of Ac/Ds makes it possible rapidly to identify the progeny which carry the gene of interest without the selective marker while at the same time facilitating the process and preventing the dissemination, by the pollen, of insufficiently characterized transgenic events.

Example 12

Construction of a Binary Plasmid, pBIOC4-FLP, which Carries the FLP Recombinase.

The sequence encoding the *Saccharomyces cerevisiae* FLP recombinase is contained in pOG44, which is marketed by Stratagene. The plasmid pOG44 was digested with the enzymes HindIII and KpnI and the HindIII-KpnI fragment was isolated. Ligation was carried out, at 14° C. for 16 hours, using 100 ng of the dephosphorylated vector pBIOS512 and 50 ng of HindIII-KpnI fragment carrying the recombinase-encoding sequence in a 10 µl reaction medium in the presence of 1 µl of 10× T4 DNA ligase buffer (Amersham) and 2.5 U of T4 DNA ligase enzyme (Amersham). *Escherichia coli* DH5α bacteria, which had previously been rendered competent, were transformed. The resulting plasmid is termed pBIOS512-FLP. The plasmid DNA harboured by the resulting clones, which were selected on medium containing 50 µg of ampicillin/ml, was extracted by the alkaline lysis method and analysed by enzymic digestion using restriction enzymes. The fragment carrying the sequence encoding the FLP recombinase was isolated by enzymic digestion with KpnI, followed by the action of the enzyme T4 DNA Polymerase (New England Biolabs) in accordance with the manufacturer's recommendations, and then digestion with HindIII. The fragment was purified by electrophoresis on an 0.8% agarose gel, after which it was electroeluted, precipitated with alcohol and dried. It was introduced at the BamHI site, which was treated with the Klenow enzyme (New England Biolabs) in accordance with the manufacturer's recommendations, and the HindIII site of the plasmid pBIOS512. The nucleotide sequence of FLP was verified by sequencing in accordance with the dideoxynucleotide method (Sanger et al., 1997) using the T7™ sequencing kit which is marketed by Pharmacia. The plasmid pBIOS512 is a derivative of pUC and carries the "35S double promoter (35SDP)—NOS terminator (NOST)" expression cassette (EcoRI fragment). The 35S double promoter originates form pJIT163 (WO 96 33277).

The EcoRI fragment carrying the "35SDP-FLP-NOST" expression cassette was isolated from pBIOS512FLP by enzyme digestion with EcoRI, after which it was purified on an 0.8% agarose gel, electroeluted, precipitated with alcohol and dried. It was introduced into the EcoRI site of pBIOC4 (WO 96 33277), which had been dephosphorylated with the enzyme calf intestinal alkaline phosphatase (Boehringer Mannheim) in accordance with the manufacturer's recommendations. The ligation was carried out, at 14° C. for 16 hours, using 100 ng of the dephosphorylated vector and 50 ng of fragments carrying the "35SDP-FLP-NOST" cassette in a 10 µl reaction medium in the presence of 1 µl of 10× T4 DNA ligase buffer (Amersham) and 2.5 u of T4 DNA ligase enzyme (Amersham). *Escherichia coli* DH5α bacteria which had been previously rendered competent were transformed. The resulting plasmid is termed pBIOC4-FLP. The plasmid DNA harboured by the resulting clones, which were selected on medium containing 12 µg of tetracycline/ml, was extracted by the alkaline lysis method and analysed by enzyme digestion using restriction enzymes. The plasmid DNA of the binary plasmid pBIOC4-FLP was introduced by direct transformation into the *Agrobacterium tumefaciens* strain LBA4404 in accordance with the method of Holsters et al. (1978). The validity of the clone which was chosen was verified by enzymically digesting the plasmid DNA which had been introduced into it.

Example 13

Construction of a Binary Plasmid, pBIOC511, which Carries Male Sterility, and Selection on Kanamycin between FRT Specific Recombination Sites, Utilizable in Tobacco Transgenesis.

The following sequences were deleted from the binary plasmid pGA492 (An, 1986): the constitutive promoter of the nos gene encoding nopaline synthase (Depicker et al., 1982), the sequence encoding the nptII gene, encoding neomycin phosphotransferase II (Berg and Berg, 1983), which sequence has been deleted of the region of the first 8 codons, including the methionine ATG start codon, and fused to the sequence of the first 14 codons of the sequence encoding the nos gene (Depicker et al., 1982), the sequence encoding the nos gene but lacking the region of the first 14 codons, and the nos terminator (Depicker et al., 1982). This deletion was carried out by total digestion with ClaI followed by partial digestion with SacII. The fragment is purified and then subjected to the action of the enzyme T4 DNA Polymerase (New England Biolabs) in accordance with the manufacturer's recommendations. The ligation of the plasmid and transformation of Escherichia coli DH5α bacteria which had previously been rendered competent, are carried out in accordance with the customary methods (Sambrook et al., 1989). The resulting plasmid is termed pBIOC506.

The FRT specific integration site was amplified by PCR from the plasmid pOG45, which is marketed by Stratagene. The two oligodeoxynucleotides employed as primers for the PCR are:

5' CCC CTG CAG TTT TCA AAA GCG CTC TGA AGT TC 3' (SEQ ID NO: 1) and

5' CCA AAG CTT GAA TTC GCC AGG GGG ATC TTG AAG TTC 3' (SEQ ID NO: 2).

The fragments which corresponded to the FRT site, and which were derived from the PCR amplification, were digested with PstI, subjected to the action of the enzyme T4 DNA Polymerase (New England Biolabs) in accordance with the manufacturer's recommendations, and then digested with EcoRI. They were purified on a 2% agarose gel, after which they were electroeluted, precipitated with alcohol, dried and taken up in water. They were then ligated between the SacI site, which had previously been subjected to the action of the enzyme T4 DNA Polymerase, and the EcoRI site of plasmid pUC18, which is marketed by Pharmacia. The resulting plasmid is termed pBIOC507.

A second FRT site was introduced into plasmid pBIOC507. This second FRT site results from carrying out a PCR amplification using the two oligodeoxynucleotides:

5' CCC CTG CAG TTT TCA AAA GCG CTC TGA AGT TC 3' (SEQ ID NO: 1) and

5' AAA GGT ACC GCC AGG GGG ATC TTG AAG TTC 3' (SEQ ID NO: 3).

The amplified fragments were digested with PstI and KpnI, subjected to the action of the enzyme T4 DNA Polymerase, and ligated in the SphI site, which had previously been treated with the enzyme T4 DNA Polymerase, of plasmid pBIOC507. The resulting plasmid is termed pBIOC508 and contains the two FRT sites oriented in the same direction.

The HindIII/EcoRI fragment carrying the two FRT sites was isolated from plasmid pBIOC508. This fragment was inserted at the HindIII and EcoRI sites of plasmid pBIOC506. The resulting plasmid is termed pBIOC509.

The SphI fragment carrying the chimeric gene corresponding to the "A9-barnase-T35S promoter" contained in pWP173 (Paul et al., 1992) was used for conferring male sterility. This SphI fragment was treated with the enzyme T4 DNA Polymerase and ligated into the PstI site, which had been treated with the enzyme T4 DNA Polymerase, of plasmid pBIOC509. The resulting plasmid is termed pBIOC510.

Finally, in order to permit selection on kanamycin (Fromm et al., 1986), the EcoRI fragment, which had been treated with the enzyme T4 DNA Polymerase and which corresponded to the "NOSP-nptII-NOST" expression cassette, isolated from a pBIOS1 plasmid into which the BamH1 fragment encoding the nptII gene had been cloned at the BamH1 site, was ligated into the KpnI site, which had been treated with the enzyme T4 DNA Polymerase, of plasmid pBIOC510. The resulting plasmid is termed pBIOC511.

Culture Media

LB
10 g of bactotryptone/l
5 g of yeast extract/l
10 g of NaCl/l
pH 7.5, adjusted with NaOH MSSV/2
2.2 g of Murashige and Skoog macro- and microelements (Sigma, cat. No. M 6899)
2 ml of Nitsch vitamins/l
15 g of sucrose/l
8 g of agar agar/l
pH 5.9, before autoclaving 2Z
4.4 g of Murashige and Skoog macro- and microelements (Sigma, cat. No. M 6899)
2 ml of Nitsch vitamins/l
30 g of sucrose/l
2 mg of zeatin/l
400 mg of Augmentin/l
100 mg of kanamycin/l
8 g of agar agar/l
pH 5.9, before autoclaving KCMS
4.4 g of Murashige and Skoog macro- and microelements (Sigma, cat. No. M 6899)
0.9 mg of thiamine/l
200 mg of potassium dihydrogen phosphate/l
30 g of sucrose/l
8 g of agar agar/l
200 µM acetosyringone
0.2 mg of 2–4D/l
0.1 mg of kinetin/l
pH 5.9, before autoclaving DEV
2.2 g of Murashige and Skoog macro- and microelements (Sigma, cat. No. M 6899)
2 ml of Nitsch vitamins/l
15 g of sucrose/l
50 mg of kanamycin/l
400 mg of Augmentin/l
8 g of agar agar/l
pH 5.8, before autoclaving MS20
4.4 g of MO4O4 (SIGMA)/l
20 g of sucrose/l
8 g of agar agar (solid medium)/l
pH 5.7
+, where appropriate, plant hormones BAP, 1 mg/l, and ANA, 0.1 mg/l MS30
4.4 g of MO4O4 (SIGMA)/l
30 g of sucrose/l
8 g of agar agar (solid medium)/l
pH 5.7
+, where appropriate, plant hormones BAP, 1 mg/l, and ANA, 0.1 mg/l

REFERENCES

An G. (1986), Plant Physiol. 81: 86–91
Bednarek S. Y. and Ralkhel N. V., The Plant Cell, 3, 1195–1206 (1991)
Broer et al., Braunschweig Symposium on Applied Plant Molecular biology, Braunschweig Nov. 21–23, (1988); Proceedings, Ed. Galling G., (1989), 240
Berg D. E., Berg C. M., (1983) Biotechnology, 1, 417–435
Close J. J., Rodriguez R. L., (1982) Gene, 20, 305–316
Cocherel S., Perez P., Degroote F., Genestier S., Picard G., (1996), Plant Molecular Biology 30: 539–551
De la Penna (1987), Nature, 325: 274–278
Depicker et al., (1982) J. Mol. Appl. Genet., 1, 561–573
Ditta G., Stanfield S., Corbin D., Helinski D. R., (1980) Pnas 77: 7347–7351
Ellstrand Norman C., (1990), Bioscience, vol. 40 No. 6, pp. 438–442
Fillatti J. J., Kiser J., Rose R. and Commaî L., (1987) Bio/Technology 5: 726–730
Finnegan E. J., Lawrence G. J., Dennis E. S., Ellis J. G., (1993) Plant Molecular Biology 22: 625–633
Franck et al., (1980) Cell, 21, 285–294
Fromm M. E., Taylor L. P., Walbot V., (1986) Nature, vol. 319, 791–793
Gaubier et al., Mol. Gen., 238, 409–418 (1993)
Holsters et al., (1978) Mol. Gen. Genet., 163, 181–187
Horsch et al., (1985), Science, 227, 1229 (1985)
Jefferson R. A., (1987) Plant Molecular Biology, Rep. 5: 387–405
Jouanin, Plant. Sci. 53, 53–63 (1987)
Kay, Science, (1987) 236, 1299–1302
Lassner M. W., Peterson P., Yoder J. I., (1989), Plant Molecular Biology Rep. 7: 116–128
Liu, (1951) Mol. Plant. Microb., Interactions, 6, 144–156
Matsuoka K., Nakamura K., (1991) Proc. Natl. Acad. Sci. USA, 88, 834–838
McElroy (1991) Mol. Gen. Genet. 231: 150–160
Murakami et al., Plant Mol. Biol., (1986) 7, 343–355
Ni et al., Plnt J., (1995) 7, 661–676
Paul W. et al. (1992) Plant. Mol. Biol. 19: 611–622
Perez P., Tiraby G., Kallerhoff J., Perret J., (1989), Plant Molecular Biology 13: 365–373
Rogers S., Bendich A. J., (1988), Plant Molecular Biology, Manual A65, 69–76
Sambrook J., Fritsch E. F., Maniatis T., (1989) Molecular cloning, a laboratory manual, 2nd edition, Cold Spring Harbor laboratory press
Sanford J. C., (1988) Trends in Biotechnology, 6, 299–302
Schroeder M. R., Borksenious O. N., Matsuoka K., Nakamura K. and Rakhel N. V., (1993) Plant. Physiol., 101, 451–458
Watson et al., recombinant DNA, Ed. De Boeck University, pp. 273–292
Weider R., Koornnef M., Zabel P., (1989) Theo. Appl. Gen., 78: 169–172
Worall D. Hird D. L., Hodge R., Paul W., Draper J., and Scott R., (1992), Plant Cell 4, 759–771
Yoder J. I. Goldsbrough A. P., (1994), Bio/Technology vol. 12, 263–267

---

The Invention claimed is:

1. A method for preventing dissemination via pollen of a transgene encoding dog gastric lipase or collagen from a transgenic plant, comprising said transgene, wherein said method comprises transforming the nuclear genome of a plant with a plasmid vector containing both a nucleic acid conferring male sterility and a transgene encoding dog gastric lipase or collagen, said transgene being genetically linked with said nucleic acid conferring male sterility, whereby said transgene is prevented from being disseminated by the pollen of said plant, and wherein said nucleic acid conferring male sterility and said transgene are each operatively linked to a transcriptional control system comprising a promoter and a transcriptional terminator.

2. The method according to claim 1, wherein said transgene encodes dog gastric lipase.

3. The method according to claim 1, wherein said promoter operably linked to the nucleic acid conferring male sterility is an anther-specific promoter.

4. The method according to claim 3, wherein the promoter is the A9 promoter.

5. A method for preventing dissemination via pollen of transgene encoding dog gastric lipase or collagen from a transgenic plant comprising said transgene, wherein said method comprises transforming the nuclear genome of a plant with a plasmid vector containing both a nucleic acid conferring male sterility and a transgene encoding dog gastric lipase or collagen, said transgene being genetically linked with said nucleic acid conferring male sterility, whereby said transgene is prevented from being disseminated by the pollen of said plant, and wherein said nucleic acid conferring male sterility and said transgene are each operably linked to a transcriptional control system comprising a promoter and a transcriptional terminator, recovering the dog gastric lipase or collagen by extraction, and administering said dog gastric lipase or collagen to a human or animal.

6. The method according to claim 5, wherein said transgene encodes dog gastric lipase.

7. The method according to claim 5, wherein the promoter operably linked to the nucleic acid conferring male sterility is an anther-specific promoter.

* * * * *

SEQUENCE LISTING

```
<160> NUMBER OF SEQ ID NOS: 9

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 1
cccctgcagt tttcaaaagc gctctgaagt tc                                    32

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 2
ccaaagcttg aattcgccag ggggatcttg aagttc                                36

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
aaaggtaccg ccaggggat cttgaagttc                                        30
```

```
<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide A9a

<400> SEQUENCE: 4
tagacattgt aggttggttt tg                                               22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide A9b

<400> SEQUENCE: 5
tctagttact tcataagttt tg                                               22

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide EM1

<400> SEQUENCE: 6
catgagcgga gaattaagg                                                   19

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide EM5

<400> SEQUENCE: 7
ttattcaggc gtagcaacca gg                                               22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide 5'H

<400> SEQUENCE: 8
aaggatcctg gcaaagacat aaatc                                            25

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Ac12

<400> SEQUENCE: 9
agatgctgct acccaatctt ttgtgc                                           26
```